United States Patent
Toma et al.

(10) Patent No.: US 8,045,147 B2
(45) Date of Patent: Oct. 25, 2011

(54) METHOD FOR DETERMINING THE SURFACE QUALITY OF A SUBSTRATE AND ASSOCIATED MACHINE FOR CONVERTING THE SUBSTRATE

(75) Inventors: Claude Toma, Crissier (CH); Jeronimo Alonso, Epalinges (CH)

(73) Assignee: Bobst S.A. (CH)

( * ) Notice: Subject to any disclaimer, the term of this patent is extended or adjusted under 35 U.S.C. 154(b) by 305 days.

(21) Appl. No.: 12/202,731

(22) Filed: Sep. 2, 2008

(65) Prior Publication Data
US 2009/0079971 A1    Mar. 26, 2009

(30) Foreign Application Priority Data
Sep. 21, 2007  (EP) .................................. 07018586

(51) Int. Cl.
*G01N 21/00*  (2006.01)
(52) U.S. Cl. .................. 356/237.2; 356/237.1
(58) Field of Classification Search .... 356/237.1–237.5; 226/45, 20; 101/484
See application file for complete search history.

(56) References Cited

U.S. PATENT DOCUMENTS

| 5,395,027 | A | 3/1995 | Erhardt | |
|---|---|---|---|---|
| 7,382,451 | B2 * | 6/2008 | Lin et al. | 356/237.5 |
| 2006/0239510 | A1 | 10/2006 | Tatarczyk et al. | |
| 2007/0006762 | A1 | 1/2007 | Jernstrom et al. | |

FOREIGN PATENT DOCUMENTS

| CA | 2 088 816 | 8/1993 |
|---|---|---|
| DE | 10 2005 026 127 A1 | 12/2006 |
| EP | 0 554 811 | 8/1993 |
| EP | 1 714 786 | 10/2006 |
| JP | 2005205853 | 8/2005 |
| JP | 2007198963 | 8/2007 |
| WO | WO 2006/131422 | 12/2006 |

OTHER PUBLICATIONS

European Search Report dated Feb. 14, 2008, issued in corresponding European Application No. 07018586.3-2304.
Japanese Office Action dated Nov. 1, 2010 in corresponding Japanese Patent Application No. JP2008-242420 (Japanese language).

* cited by examiner

*Primary Examiner* — Tri T Ton
(74) *Attorney, Agent, or Firm* — Ostrolenk Faber LLP

(57) ABSTRACT

A method for determining the surface quality of a substrate passing from an initial state into a converted state during a conversion process including the steps of acquiring first information relating to surface defects detected on the initial substrate, acquiring second information relating to surface defects detected on the converted substrate, of processing the first information and the second information, and of classifying the converted substrate as a function of the first acquired information relating to the surface defects detected on the initial substrate and as a function of the second acquired information relating to the surface defects detected on the converted substrate.

10 Claims, 2 Drawing Sheets

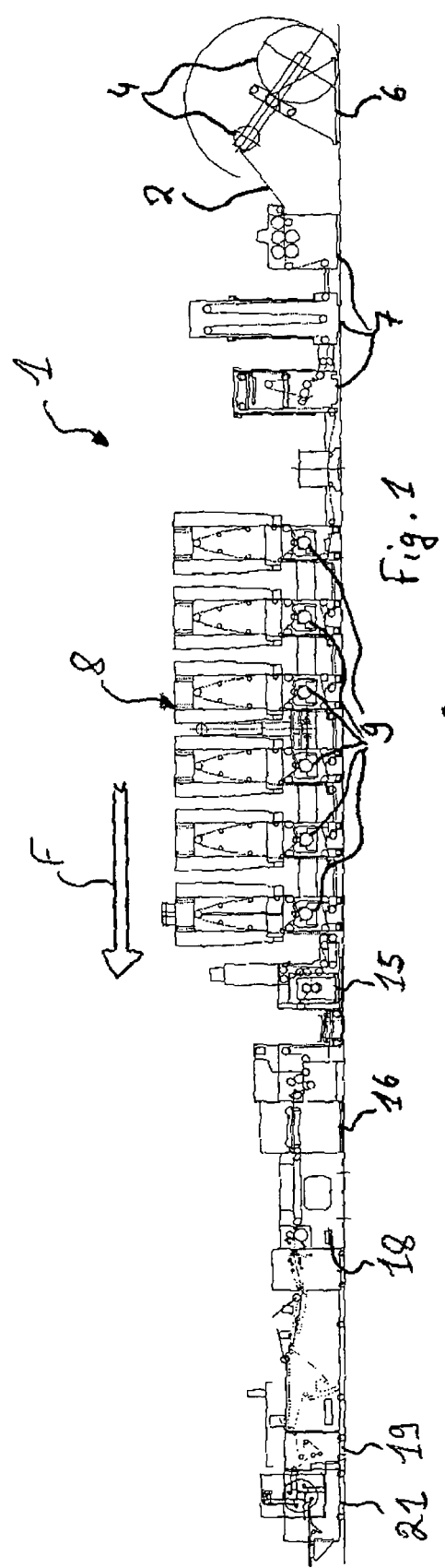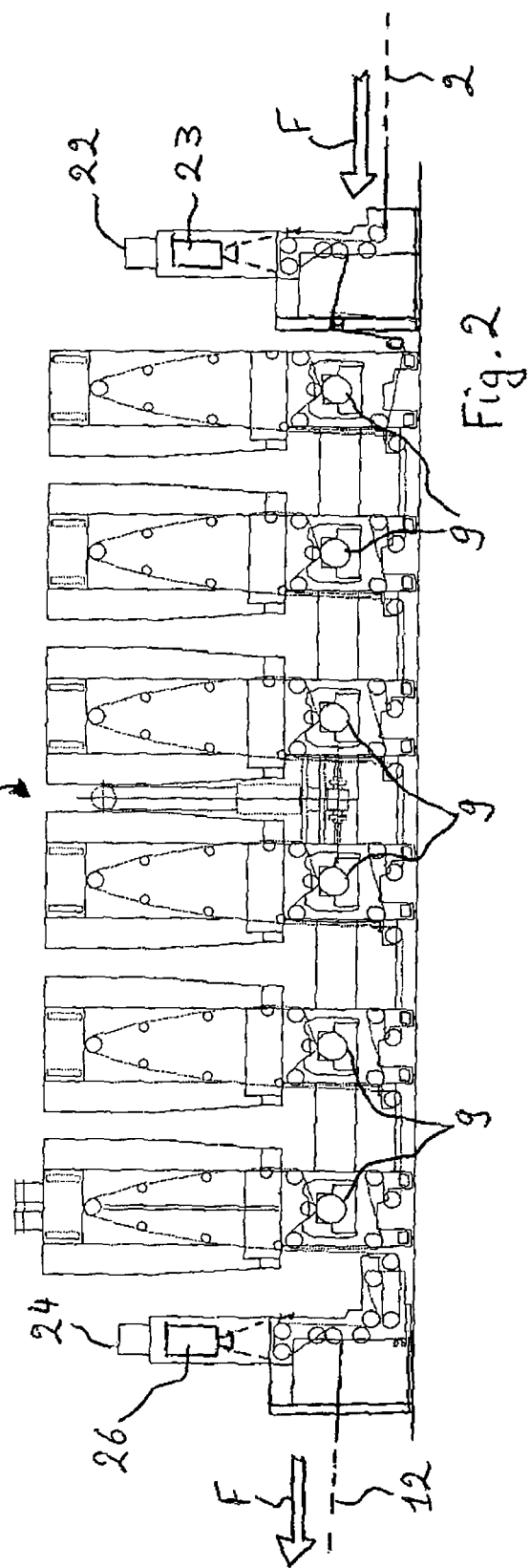

METHOD FOR DETERMINING THE SURFACE QUALITY OF A SUBSTRATE AND ASSOCIATED MACHINE FOR CONVERTING THE SUBSTRATE

BACKGROUND OF THE INVENTION

The present invention relates to a method for determining the surface quality of a substrate. This substrate passes from an initial state into a converted state. The invention also relates to a substrate-converting machine for converting an initial substrate and obtaining a converted substrate. The substrate-converting machine is part of a packaging production line.

In the packaging industry, a production line delivers a converted product produced from an initial substrate introduced at the start. The substrate may be a virgin substrate. More often than not, the virgin initial substrate may undergo a conversion process, for example by being printed on in a printing process, or in embossing, creasing and/or cutting operations, in order to obtain blanks or boxes corresponding to the packaging when it is laid out flat.

The initial substrate in the form of a reel undergoing a conversion process may have already previously undergone one or more prior treatments and then been reconditioned, for example in the form of a new reel. In this case, an insetting operation is necessary for the following conversion process.

The converting machine comprises one or more elements. Each of these elements is capable of giving rise to various defects on the surface of the converted substrate, leading to quality concerns for the packaging produced.

Checking the print quality proves to be a necessary operation when the packaging manufacturer wishes to be able to ensure that a production batch will not be spoiled by defects. These defects are assessed according to various acceptability criteria, but the selection of packaging is mainly made according to a quality level criterion chosen as a function of the product that has to be packaged.

Checking the substrate after conversion, before or after cutting, with close observation of the converted substrate, of the blanks or of the boxes, is still currently carried out by eye. The operator searches for all the types of defect, for example those associated with printing, and adjusts the settings of the converting machine as a result, so as to eliminate or limit these defects, preferably as quickly as possible.

This checking is increasingly frequently carried out automatically on the production line. The blanks or boxes that do not comply with the minimum requirements of printing and/or cutting and/or creasing and/or embossing quality in relation to a sample considered to be free of defects are ejected before they are stacked in the receiving station. The device for automatically detecting defects is located following the final converting element, before the ejection station and before the cutting station.

In the case of what is known as a reel-to-reel application, that is to say one starting from a reel of initial substrate and leading to another reel, of converted substrate, a converted substrate which does not comply with the minimum requirements of printing and/or creasing and/or embossing quality in relation to a sample considered to be free of defects is identified and may be singled out.

PRIOR ART

Numerous devices for viewing and/or detecting these defects exist. They generally use a video camera or any other equipment for collecting the light reflected by the printed substrate.

By way of example, EP 0,554,811 describes a device for detecting printing errors, and therefore also defects, on a substrate in web or sheet form moving through a printing machine. The device comprises a first camera for recording, at a first resolution, an image of a sample area of the print on the substrate and an electronic computerized device for digitizing the image and then comparing it with a prerecorded reference image. A second camera for recording the overall print at a second resolution lower than the first is linked to the first camera. The comparative results obtained from the second camera are used in a feedback loop to check the operation of the first camera.

However, such a device is unable to identify all types of defects. In fact, some defects will be progressively masked by the printing of successive colors as the substrate passes through successive printing units. As a result, these defects will not be identified on the surface of the printed substrate. The printed substrate will be classed as being acceptable for forming packaging, while in reality a quick visual check would allow the imperfections to be detected.

U.S. Pat. No. 5,395,027 discloses a device for monitoring a continuous substrate, to be precise a paper substrate, moving through a printing machine. By means of this device, it is possible to determine whether the substrate is moving correctly, with the correct tension, and has no tears or fissures. Such defects in the substrate cause damage to the printing machine and to its accessories as the substrate passes through this machine. Such a device triggers a warning signal and serves to control an arrangement for limiting the damage. The arrangement removes all or part of the defective substrate from the printing machine.

However, such a device is only able to prevent damage to the printing machine caused by a defective substrate giving rise to jamming of the substrate during printing. The device is not designed to check the state and quality of the substrate at the end of the printing process. The use of such a device only makes it possible to prevent efficiency drops by limiting the number of times the printing machine stops. The use of such a device has no effect on the final quality of the printed substrate.

SUMMARY OF THE INVENTION

One main problem to be solved by the invention consists in providing a method for determining the surface quality of a substrate subjected to a conversion process. A second problem is to further improve the quality of the substrate exiting a conversion process by systematically detecting its defects. A third problem is to provide a multistep method during which the substrate, as it passes from an initial state to a converted state, undergoes quality control checks. A fourth problem is to increase the number of steps of searching for defects in order to provide a converted substrate of optimum quality, depending on the user's wishes. A fifth problem is that of implementing a method of determining the quality of a substrate while avoiding the problems of the prior art. Yet another problem is that of providing a converting machine that allows the information regarding the defects detected to be processed.

The invention thus relates to a method for determining the surface quality of a substrate passing from an initial state into a converted state during a conversion process, the method comprising the steps of acquiring first information relating to surface defects detected on the initial substrate, acquiring second information relating to surface defects detected on the converted substrate, processing the first information and the second information, and classifying said converted substrate as a function of the first information acquired relating to the surface defects detected on said initial substrate and as a function of the second information acquired relating to the surface defects detected on said converted substrate.

Throughout the description, the substrate is defined as being in the form of a continuous web, for example of paper, cardboard or plastic, such as polyethylene terephthalate (PET), biaxially oriented polypropylene (BOPP), etc., or aluminum, or in the form of a sheet, for example of flat board or corrugated board, or else a flexible material, such as polyethylene (PE).

The initial substrate is defined as being an unprocessed, virgin substrate output by the machine for producing said substrate and lacking any printing, marking, creasing, embossing, gluing, etc. This virgin substrate may be provided with a coating, for example a white, etc. This virgin substrate may also be a pasted-paper or laminated substrate.

The initial substrate is also defined as being a substrate that has undergone a first prior conversion process, such as a first printing, a first embossing, etc.

The converted substrate is defined as being a substrate that has undergone a conversion process. The conversion process may be a printing process, during which one or more colors were applied to the surface of the substrate, in order to apply graphics thereto and/or to give it an esthetic appearance. The conversion process may also be a creasing, embossing, structuring or hot foil stamping process or a process for adhesively gluing labels or holograms, etc. This converted substrate may include a layer of lacquer covering all or part of the printed surface.

The surface defects detected on the initial substrate are defined, by way of nonlimiting examples, as being holes, tears, stains (machine oil), streaks, dust, coarse wood fibers, areas of coating pick, etc.

The surface defects detected on the converted substrate are defined, by way of nonlimiting examples, as being doctor blade streaks, smudges, stains, undesirable lines, background transitions, variations in color strength due to a lack or surplus of ink, missing print, printing plates becoming detached from cylinders, bad line-ups, when the defect results from a shifting between the various printing colors, or even a maladjustment of the electric line shaft for setting a plurality of colors with respect to one another, registration errors between the color or colors printed and the embossing or hot-foil stamping, etc.

In other words, by adding a detection step before conversion to a detection step after conversion, all the information acquired will enable the quality control of the final product to be improved. The method makes it possible to separate the defects in the material that are present on the initial substrate from the conversion defects present on the surface of the converted substrate, in order to optimize the handling of the defects detected.

By linking two defect detection steps, the converted substrate obtained will be classified into various categories. The packaging manufacturer may thus choose to keep a converted substrate, blank or box with defects that are apparently only initial-substrate defects, converted-substrate defects, or both.

By virtue of this solution, the production quality can be 100% guaranteed, thus avoiding returned sets of blanks or boxes that are spoiled by defects to the packaging manufacturer. By virtue of this solution, the production quality can be 100% guaranteed, authorizing the return of the initial substrate to the manufacturer of said initial substrate if the latter is detected as having too many defects.

This substrate or these substrates spoiled by errors and therefore classified the operator to make an imsubstratete decision regarding the setting of the converting machine. Indeed, if the same defect is detected simultaneously at the same location on the initial substrate and on the converted substrate, the settings of the converting machine do not need to be modified since the defects cannot be corrected because of their origin.

According to another aspect of the present invention, a converting machine for converting an initial substrate and obtaining a converted substrate, comprises:

at least one element for converting the initial substrate, a first device for detecting surface defects on said initial substrate and acquiring first information relating to the surface defects detected on said initial substrate, said device being placed upstream of the converting element or elements, a second device for detecting surface defects on the converted substrate and acquiring second information relating to the surface defects detected on said converted substrate, said device being placed downstream of the converting element or elements, and a unit processing the first information and the second information and classifying said converted substrate as a function of the acquired information relating to said surface defects detected on said initial substrate and as a function of the acquired information relating to said surface defects detected on said converted substrate.

The converting element is defined by way of nonlimiting examples as being a printing machine, for example a photogravure printing machine having at least one printing unit, a flexography printing machine or an offset printing machine, or an embossing unit, a creasing unit, or a hot foil stamping unit, etc.

The terms "upstream" and "downstream" are defined in relation to the direction of movement of the substrate during conversion.

In other words, the processing unit allows the operator to view the types of defects detected. The processing unit could also be connected to an ejection station which allows blanks or boxes to be eliminated according to various criteria, initial-substrate defect or conversion defect, at the choice of the packaging manufacturer. The converting machine is integrated into a packaging production line.

BRIEF DESCRIPTION OF THE DRAWINGS

The invention will be understood better and its various advantages and features will become apparent from the following description by way of nonlimiting exemplary embodiments and with reference to the attached schematic drawings, in which:

FIG. 1 shows a side elevation of a packaging production line according to the prior art;

FIG. 2 shows a side elevation of a printing machine according to the invention.

DETAILED DESCRIPTION OF THE PREFERRED EMBODIMENTS

Figure 3:
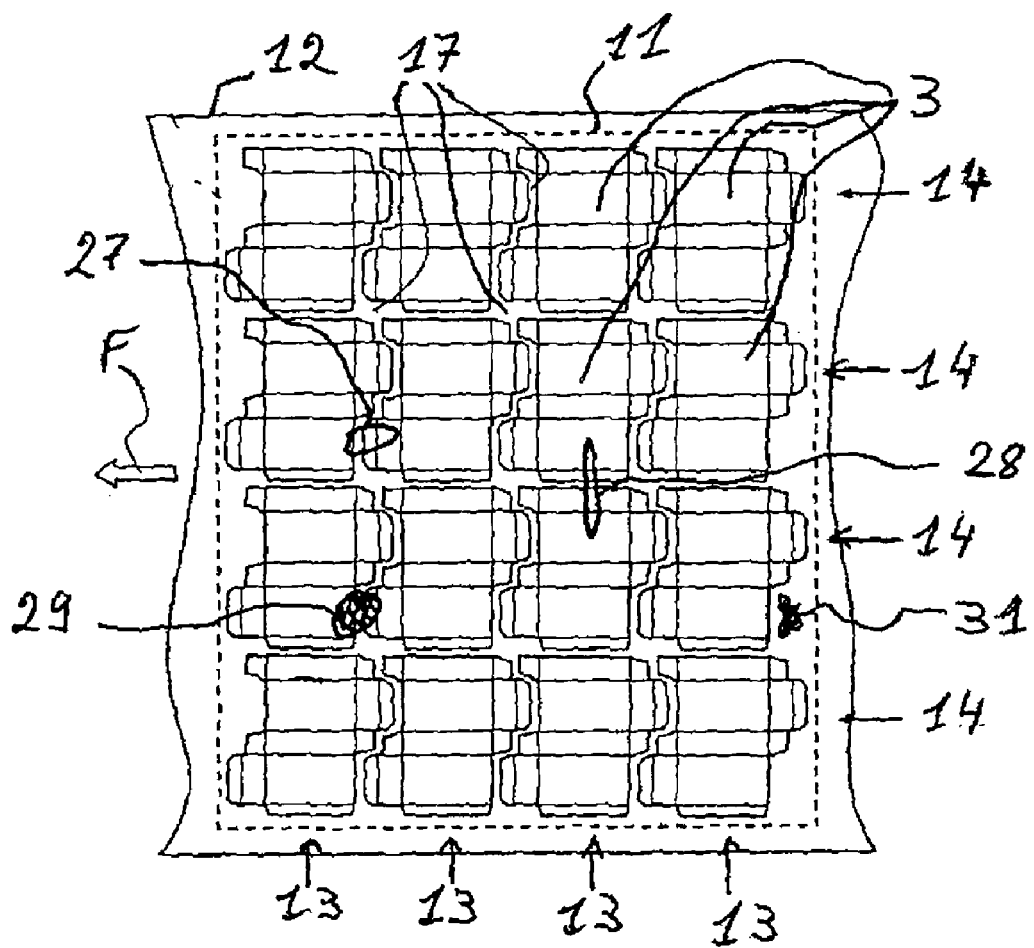
FIG. 3 shows a plan view of a printed web portion.

As illustrated in FIGS. 1 and 2, the production of packaging is implemented on a packaging production line (1). This production commences with an initial continuous substrate, i.e. a virgin web (2), for example of paper board and passes through various successive phases, described generally hereinafter. The packaging production line (1) is intended for the manufacture of boxes (3) that are able to be formed into packaging by folding and gluing.

In a first phase, a reel (4) of this virgin web (2) is unreeled by means of a web unwinder (6) that holds the reels (4). An infeed station (7) then allows the tension in the virgin web (2) to be regulated and to be forwarded to a converting machine, described in an example here as a printing machine (8). The direction of advance (arrow F in FIGS. 1 to 3) of the virgin web (2) provides the upstream and downstream directions.

In a second phase, the virgin web (2) is printed and then dried as it passes through the printing machine (8). The web (2) passes successively through a plurality of printing units (9), in this case six, in order for printing to be carried out.

The virgin web (2) is printed with a blank (11), shown in dotted line in FIG. 3, during each complete revolution of the printing cylinders of the various printing units (9). Each blank (11) comprises one or more boxes (3) in developed form. By way of example, a blank (11) including sixteen boxes (3) with their future folding and cutting lines is shown in FIG. 3. The converted substrate, i.e. the printed web (12), is wide enough to contain a plurality of generally identical boxes (3). The boxes (3) are arranged in columns (13) and rows (14) in accordance with the direction of movement (F) of the printed web (12).

An embossing station (15) is provided following the printing machine (8).

In a third phase, the printed web (12) is forwarded to a flat-bed die-cutting station (16) which cuts all the blanks (11) or boxes (3) from the rest of the printed web (12). The flat-bed die-cutting station (16) subsequently generates intersubstrate waste (17). The intermediate scrap (17) is removed in a waste stripping station (18).

In a fourth phase, the blanks (11) or boxes (3) are then shingled before being stacked by rows in order to form stacks in a delivery station (19). The stacks are palletized in a palletizing station (21) with a view to storing or transporting them outside the production line (1).

According to the invention implemented on the packaging production line (1) and more particularly on the printing machine (8), the aim of the method is to determine the surface quality of the web passing from its virgin state (2) to its printed state (12). FIG. 2 gives an example of the implementation thereof In a first step of this method, first information relating to surface defects detected on the virgin web (2) is acquired. This first step may comprise two additional substeps. These two substeps may be provided preceding the conversion process, in this case printing. The first of these two substeps may comprise detecting surface defects on the initial substrate formed by the virgin web (2). The second of the two substeps may comprise generating first information relating to the surface defects on the initial substrate formed by this virgin web (2).

In the preferred exemplary embodiment, the virgin web (2) enters a first quality control station (22) fitted in or at the exit of the infeed station (7) and before the first printing unit (9) of the printing machine (8). The first quality control station (22) is operable to detect, recognize and take account of all the types of defects and thus to verify that this virgin web (2) has no defects.

The first quality control station (22) is equipped in particular with a first device which examines the virgin web (2) and detects defects on the surface thereof This first device is in the form of a viewing system, such as one or more high-resolution cameras (23) provided with corresponding illumination means. By comparison with an example stored in memory and defined as a model, it is determined whether the virgin web (2) is spoiled by a defect. If it is spoiled, a checking device in this first quality control station (22) can work out the coordinates of the defect detected.

In a variant embodiment of the first step, the two additional substeps which may be located and performed preceding conversion process, in this case printing, may comprise detecting the surface defects on initial substrate formed by the virgin web (2), and may comprise generating first information. The substeps may be implemented by a manufacturer of the initial substrate formed by the virgin web (2). The first information is included in a first file. The manufacturer of the initial substrate provides the packaging manufacturer with the virgin web (2) on a reel (4), accompanied by the first file containing the first information listing all the defects detected, including in particular their position and nature.

Each of the printing units (9) of the printing machine (8) is liable to generate various defects on the surface of the printed web (12). In a second step of this method, second information relating to surface defects detected on the printed web (12) is acquired. This second step may include two additional substeps. These two substeps may be located and performed following the conversion process, in this case printing. The first of these two substeps may comprise being able to detect the surface defects on the converted substrate formed by the printed web (12). The second of these two substeps may comprise generating second information relating to the surface defects on the converted substrate formed by this printed web (12).

In the preferred exemplary embodiment, the printed web (12) enters a second quality control station (24) fitted at the exit of the last printing unit (9) of the printing machine (8) and before the cutting station (16). The second quality control station (24) is operable to detect, recognize and take account of all the types of defect and thus to verify that this printed web (12) has no defects.

The second quality control station (24) is equipped in particular with a second device which examines the entire surface of the printing format (11) of the printed web (12) and detects defects on the surface thereof This second device is in the form of a viewing system, such as one or more high-resolution cameras (26) provided with corresponding illumination means. By comparison with a format stored in memory and defined as a model, it is determined whether the portion of printed web (12) is spoiled by a defect. If it is spoiled, the checking device in this second quality control station (24) can work out in which column (13) and in which row (14) of the printing format (11) the defect has been detected.

In another variant embodiment of the second step, the two additional substeps, which may be located and performed following the conversion process, in this case printing, may comprise detecting the surface defects on the converted substrate formed by the printed web (12), and may comprise generating second information. These substeps may be implemented by a user of the converted substrate formed by the printed web (12). The second information is included in a second file. The user of the converted substrate receives from the packaging manufacturer the converted substrate formed by the printed web (12) on a reel, accompanied by the second file containing the second information listing all the defects detected, including in particular their position and nature.

In a third step, of the method, the first and second information are processed and compared with each other by means of a specific computing unit (not shown). The defects are identified and stored in memory by the unit which records their position in relation to an origin, in the longitudinal direction, and in relation to the different rows (14) they occupy, in the transverse direction.

In a fourth step of the method, this printed web (12) is classified as a function of the first acquired information relating to the surface defects detected on this virgin web (2) and as a function of the second acquired information relating to the surface defects detected on this printed web (12).

The method for determining the surface quality of the substrate is also a handling method and a decision-making tool. It makes it possible in particular to locate, for example in schematic, tabular, digital-file or image form, the whole of the substrate such as the printed web (12) spoiled by all of its previously detected defects.

By virtue of the method, several scenarios representing the quality level of the virgin and printed web (2 and 12) can be viewed. All the portions of the virgin and printed web (2 and 12) covered by very pronounced defects, which it would be advisable to eliminate, are counted and identified in each case. The method is implemented before even carrying out an irreversible cutting, ejecting or conditioning action on the blanks (3).

The method may preferably comprise an additional step, performed and located following the step of classifying the printed substrate. This step may comprise marking all or part of the converted substrate formed by the printed web (12) such that the surface defects detected on the initial substrate formed by the virgin web (2) and/or the surface defects detected on the converted substrate formed by the printed web (12) are identified.

Advantageously, the method may comprise an additional step, performed and located following the fourth step of classifying this converted substrate formed by the printed web (12).

The method makes it possible to distinguish and separate out the defects (27) acquired or detected by the first quality control station (22) but not acquired or not detected by the second quality control station (24). If the print is acceptable, the printing machine (8) continues its production batch which will be forwarded to the following cutting station (16). In this case, the defects (27) present on the virgin web (2) have been masked by a high color density during the conversion process, i.e. printing.

These defects (27) are considered acceptable by some packaging manufacturers depending on the type of product packaged. Depending on their nature, these defects (27) may be eliminated by removing dust from the virgin web (2). Depending on their density, these defects (27) may also lead to the reel (4) being returned to the manufacturer of the virgin web (2).

The method makes it possible to distinguish and separate out the defects (28) acquired or detected by the second quality control station (24) but not acquired or not detected by the first quality control station (22). These are defects (28) which generally result from one of the members of the rotary press becoming worn or drifting and which can only increase during printing.

If the print is not acceptable, the operator of the printing machine (8) will be informed and will make the necessary changes to the controls of the printing machine (8) in order to correct the defect (28). If necessary, the operator of the printing machine (8) will even be forced to stop printing in order to fix the possible cause of the defect (28) before it becomes unacceptable. To start with, these defects (28) remain temporarily within tolerance limits but constitute a warning of deterioration in progress. These defects (28) are frequently due to progressive wear of a plurality of parts of the printing machine (8), such as, conventionally, the ink doctor blade, the printing form, the pressure roller, etc. Such defects (28) may also be the result of dust being momentarily deposited, which can easily be removed.

The method makes it possible to distinguish and separate out the defects (29) acquired or detected by the first quality control station (22) and by the second quality control station (24). These transient and very significant defects require the printed web (12), the blanks (11) or the boxes (3) to be subsequently withdrawn from the line (1) for scrap.

The registering of these defects (29) involves intervention by the operator of the printing machine (8) or the use of an automatic labeling machine to mark the approximate location where the defect (29) has been detected. This marking takes place by placing a tab of board on the printed web (12) such that the tab protrudes slightly from its edge and can easily be identified if the printed web (12) is rewinded again.

This classification step with these defects (29) being registered also means that an ejection station (not shown) for ejecting all or part of the printed web (12), the blanks (11) or the boxes (3) with corresponding defects is operated.

In a complete version, the first information relating to surface defects detected on the initial substrate formed by the virgin web (2) and the second information relating to surface defects detected on the converted substrate formed by the printed web (12) may advantageously be acquired from the front and reverse sides of the initial substrate formed by this virgin web (2) and then from this printed web (12).

It should be noted that, if the defect monitoring resolution so allows, the first information relating to the surface defects (31) detected on the initial substrate or on the virgin web (2) and the second information relating to the surface defects detected on the converted substrate or on the printed web (12), corresponding to defects located in the waste areas (17) after cutting, can be singled out.

The present invention is not limited to the embodiments described and illustrated. Numerous modifications may be carried out without departing from the scope of protection defined by the scope of the set of claims.

The production line (1) shown uses an initial web (2) on a reel and a cutting station (16). However, the production line (1) could use an initial web (2) on a reel (4) and then a station for rewinding the printed web (12), i.e. the converted substrate, the latter station being located at the end of the line and with no cutting station or station for ejecting the blanks or boxes considered not to comply with the requirements being included.

The present invention also relates to a production line using large format sheets as printing substrate rather than a web and using a flat-bed die-cutting platen rather than a rotary cutting member.

The invention claimed is:

1. A method for determining the surface quality of a substrate passing from an initial state of an initial substrate into a converted state of a converted substrate during a conversion process in a substrate-converting machine in a packaging production line, the method comprising the steps of:

prior to performing the conversion process of the initial substrate in the substrate-converting machine in the packaging production line, acquiring first information relating to surface defects detected on the initial substrate, after performing the conversion process of the initial substrate in the substrate-converting machine, acquiring second information relating to surface defects detected on the converted substrate, processing the first information and the second information by a processing unit, and classifying the converted substrate by the processing unit as a function of the first acquired information relating to the surface defects detected on the initial substrate and as a function of the second acquired information relating to the surface defects detected on the converted substrate, wherein the classifying distinguishes the surface defects detected on the initial substrate from the surface defects detected on the converted substrate.

2. The method according to claim 1, further comprising the steps following the conversion process of: detecting the surface defects on the converted substrate and creating second information relating to the surface defects on the converted substrate.

3. The method according to claim 2, wherein the additional steps following the conversion process, of detecting the surface defects on the converted substrate and of generating second information, are implemented by a user of the converted substrate.

4. The method according to claim 1, further comprising two additional steps, preceding the conversion process, of detecting the surface defects on the initial substrate and of creating first information relating to said surface defects on said initial substrate.

5. The method according to claim 4, wherein the two additional steps preceding the conversion process, of detecting the surface defects on the initial substrate and of generating first information, are implemented by a manufacturer of the initial substrate.

6. The method according to claim 1, further comprising an additional step, following the step of classifying the converted substrate, of marking all or part of the converted substrate identifying at least one of the surface defects detected on the initial substrate and the surface defects detected on the converted substrate.

7. The method according to claim 1, further comprising an additional step, following the step of classifying the converted substrate, of ejecting all or part of the converted substrate.

8. The method according to claim 2, further comprising acquiring the first information relating to surface defects detected on the initial substrate and the second information relating to surface defects detected on the converted substrate from a front side and a reverse side of the initial substrate and of the converted substrate.

9. A converting machine for converting an initial substrate and obtaining a converted substrate in a packaging production line, comprising:

at least one element for converting the initial substrate, a first device for detecting surface defects on said initial substrate and acquiring first information relating to the surface defects detected on the initial substrate, the first device being placed upstream of the at least one converting element in a path of the substrate through conversion in the packaging production line, a second device for detecting surface defects on the converted substrate and acquiring second information relating to the surface defects detected on the converted substrate, the second device being placed downstream of the at least one converting element, and a unit operable for processing the first information and the second information and classifying the converted substrate as a function of the acquired information relating to the surface defects detected on the initial substrate in a path of the substrate through conversion and as a function of the acquired information relating to the surface defects detected on the converted substrate, wherein the classifying distinguishes the surface defects detected on the initial substrate from the surface defects detected on the converted substrate.

10. The machine according to claim 9, wherein the first device for detecting surface defects on the initial substrate and the second device for detecting surface defects on the converted substrate comprise a viewing system provided with an illuminating device operable for illuminating the substrate.

\* \* \* \* \*